United States Patent
Hu et al.

(10) Patent No.: US 7,151,206 B2
(45) Date of Patent: Dec. 19, 2006

(54) ARABIDOPSIS ARGOS, A NOVEL GENE INVOLVED IN ORGAN DEVELOPMENT

(75) Inventors: Yuxin Hu, Singapore (SG); Qi Xie, Singapore (SG); Nam-Hai Chua, New York, NY (US)

(73) Assignee: Temasek Life Sciences Laboratory, Singapore (SG)

(*) Notice: Subject to any disclaimer, the term of this patent is extended or adjusted under 35 U.S.C. 154(b) by 316 days.

(21) Appl. No.: 10/715,129

(22) Filed: Nov. 18, 2003

(65) Prior Publication Data

US 2005/0108793 A1    May 19, 2005

(51) Int. Cl.
    *C12N 15/29*    (2006.01)
    *C12N 15/82*    (2006.01)
    *C12N 5/04*     (2006.01)
    *A01H 5/00*     (2006.01)
    *A01H 5/10*     (2006.01)

(52) U.S. Cl. .................. 800/298; 800/287; 800/278; 800/290; 435/320.1; 435/419; 536/23.1; 536/23.6

(58) Field of Classification Search ............... 536/23.1, 536/23.6; 435/320.1, 419, 468; 800/278, 800/298, 287, 290
    See application file for complete search history.

(56) References Cited

OTHER PUBLICATIONS

Bowie et al, Science 247:1306-1310, 1990.*
McConnell et al, Nature 411 (6838):709-713, 2001.*
Chen et al (Sep. 1999, NCBI Accession No. AI998680).*
Autran, D., Jonak, C., Belcram, K., Beemster, G.T.S., Kronenberger, J., Grandjean, O., Inzé, D., and Traas, J. (2002). Cell numbers and leaf development in *Arabidopsis*: a functional analysis of the *STRUWWELPETER* gene, EMBO J. 21, 6036-6049.
Casimiro, I., Marchant, A., Bhalerao, R.P., Beeckman, T., Dhooge, S., Swarup, R., Graham, N., Inzé, D. Sandberg, G., Casero, P.J., and Bennett, M. (2001). Auxin transport promotes *Arabidopsis* lateral root initiation. Plant Cell 13, 843-852.
Dharmasiri, S. And Estelle, M. (2002). The role of regulated protein degradation in auxin response. Plant Mol. Biol. 49, 401-409.
Donnelly, P.M. Bonetta, D., Tsukaya, H., Dengler, R.E., and Dengler, N.G. (1999). Cell cycling and cell enlargement in developing leaves of *Arabidopsis*. Dev. Biol. 215, 407-419.
Ecker, J.R., (1995). The ethylene signal transduction pathway in plants. Science 268, 667-675.
Golz, J.F. and Hudson, A. (2002). Signaling in plant lateral organ development. Plant Cell 14, S277-S288.
Leyser, H.M., Lincoln, C.A., Timpte, C., Lammer, D., Turner, J., and Estelle, M. (1993). *Arabidopsis* auxin-resistance gene AXR1 encodes a protein related to ubiquitin-activating enzyme E1. Nature 364, 161-164.
Leyser, O. (2002). Molecular genetics of auxin signaling. Annu. Rev. Plant Biol. 53, 377-398.
Lincoln, C., Britton, J.H., and Estelle, M. (1990). Growth and development of the axr1 mutants of *Arabidopsis*. Plant Cell 2, 1071-1080.
Mizukami, Y. (2001). A matter of size: developmental control of organ size in plants. Curr. Opin. Plant Biol. 4, 533-539.
Mizukami, Y. and Fischer, R.L. (2000). Plant organ size control: *AINTEGUMENTA* regulates growth and cell numbers during organogenesis. Proc. Natl. Acad. Sci. USA 97, 942-947.
Talbert, P.B., Adler, H.T., Parks, D.W., and Comai, L. (1995). The *REVOLUTA* gene is necessary for apical meristem development and for limiting cell divisions in the leaves and stems of *Arabidopsis thaliana*. Development 121, 2723-2735.
Timpte, C.C., Wilson, A.K., and Estelle, M. (1992). Effects of the axr2 mutation of *Arabidopsis* on cell shape in hypocotyl and inflorescence. Planta 188, 271-278.
Xie, Q., Frugis, G. Colgan, D., and Chua, N.H. (2000). *Arabidopsi* NAC1 tranduces auxin signal downstream of TIRI to promote lateral root development. Genes Dev. 14, 3024-3036.
Xie, Q, Guo, H.S., Dallman, G., Fang, S., Weissman, A.M., and Chua, N.H. (2002). SINATS promotes ubiquitin-related degradation of NAC1 to attenuate auxin signals. Nature 419, 167-170.

* cited by examiner

*Primary Examiner*—Stuart F. Baum
(74) *Attorney, Agent, or Firm*—Rothwell, Figg, Ernst & Manbeck (57) ABSTRACT

The present invention is directed to a novel auxin-inducible gene, ARGOS, that is involved in organ development, including size control, in plants. Methods of influencing this development are also described, as are transformed cells and transgenic plants comprising the described sequences.

40 Claims, 6 Drawing Sheets

A

```
CTTGTCTTCCTCATTTCCCTACTAGTACTTGTTTCACACAGTTTCTTGATCCAACCAAAACCAATACACAAAGCTTCTCA  80
AACTCCTTCACCTCAAAGCTTCTTCCTTTACATCTGAATCGTTGAGTTAACTCGGATTTGTTCTGCATCCTCTGTTTCTG 160
AATCGTGGGCCATCCTTATTTTGTCTCGAATTCTTCACCAATTGCTTCGATCAAGCTGCATTGGTTAACCAGTTGCCCTA 240
AAGATCAGATCTTTGAGCAAAATTTTGTCACTGATCTTCTAAATCCAAACCAGACACAGCAAAACAACCTCTGTAATGAT 320
TCGAGAAATCTCAAACTTACAAAAAGATATTATAAACATTCAAGACAGTTATTCGAACAACCGAGTC ATG GAC GTC  396
                                                                   M   D   V   3
```

```
GGA AGA AAC AAC CGG AAA AAC ATG AGC TTT CGA AGT TCG CCG GAG AAA AGC AAG CAA GAG 456
 G   R   N   N   R   K   N   M   S   F   R   S   S   P   E   K   S   K   Q   E  23
TTA CGG CGG AGT TTC TCG GCG CAG AAA AGG ATG ATG ATC CCG GCG AAT TAT TTC AGT TTA 516
 L   R   R   S   F   S   A   Q   K   R   M   M   I   P   A   N   Y   F   S   L  43
GAG TCT CTG TTC CTA TTG GTT GGT CTA ACG GCA TCT CTG TTA ATA CTT CCG TTA GTT TTG 576
 E   S   L   F   L   L   V   G   L   T   A   S   L   L   I   L   P   L   V   L  63
CCG CCG TTA CCT CCG CCT CCG TTT ATG CTG CTA TTG GTT CCC ATT GGG ATT ATG GTT TTA 636
 P   P   L   P   P   P   P   F   M   L   L   V   P   I   G   I   M   V   L      83
CTC GTC GTT CTT GCC TTC ATG CCT TCT TCT CAT TCT AAT GCT AAT ACA GAT GTA ACT TGC 696
 L   V   V   L   A   F   M   P   S   S   H   S   N   A   N   T   D   V   T   C 103
AAT TTC ATG TAA ATCTGAAATTTATTATATGATGAT                                         732
 N   F   M   *                                                                   106
```

ARABIDOPSIS ARGOS, A NOVEL GENE INVOLVED IN ORGAN DEVELOPMENT

FIELD OF THE INVENTION

The present invention relates generally to genetic manipulation of plants, and, more particularly, to regulating organ development in transformed plants and plant cells.

BACKGROUND OF THE INVENTION

Throughout this application, various publications are referenced within parentheses. Disclosures of these publications in their entireties are hereby incorporated by reference into this application to more fully describe the state of the art to which this invention pertains. Full bibliographic citations for the references may be found listed immediately preceding the claims.

In plants, the developmental control of morphogenesis entails the coordination of cell growth, cell division and cell differentiation, and undoubtedly, organ size is one of the most obvious reflections of this coordination (Mizukami, 2001). Organ size is determined both by cell size and cell number. Genetic studies have revealed that differences in cell size or cell polar elongation apparently contribute to the size difference of plant organs (Kim et al., 1998; Kondorosi et al., 2000; Kim et al., 2002). On the other hand, larger organs tend to contain more cells than smaller ones, implying that cell division plays a fundamental role in organ size determination during organogenesis. Some mutants with altered organ size, such as struwwelpeter (swp) and phantastica (phan) (Waites et al., 1998; Autran et al., 2002), indeed show a decreased or increased cell number in their organs. However, there are cases in which alteration of cell proliferation is not always correlated with changes in organ size. For example, expression of a dominant-negative *Arabidopsis* CDKA in tobacco results in the almost normal size of leaves with fewer but larger cells (Hemerly et al., 1995). In *Arabidopsis*, over-expression of CycD3;1,a G1 cyclin gene, fails to increase organ size, leading to a disturbed organogenesis with numerous small, incompletely differentiated cells (Riou-Khamlichi et al., 1999; Dewitte et al., 2003). Similar data were obtained from over-expression of E2Fa and DPa, two transcriptional factors that play a role in activating cell division gene. Co-expression of E2Fa and DPa in *Arabidopsis* causes extra cell division but early arrested growth of plants (De Veylder et al., 2002). These observations suggest the existence of an intrinsic mechanism to coordinate cell proliferation and growth, by which the organ development is strictly controlled (Beemster et al., 2003).

The aerial organs in plant come from the promordia initiated from apical and lateral meristems. Significant changes in morphology and size of organs occur when the specification or growth of these meristems or primordia is disorganized or interrupted. A considerable number of genes involved in this developmental process has been identified and characterized, such as *WUSCHEL* (*WUS*), *CLAVATAs* (*CLVs*), *and SHOOT MERISTEMLESS* (*STM*) (Meyerowitz, 1997; Golz and Hudson, 2002). Nevertheless, lateral organ growth appears to rely on the interactive and durable division of cells within organ or organ meristems (Mizukami, 2001). Although cells in plant organs remain theoretically in an indeterminate dividing state or even a differentiated cell in plant can revert to a stem cell (Weigel and Jugens, 2002), the determinate organ growth destines these cells to stop dividing as an organ develops. Thus, cell meristematic competence appears to be critical to the cell proliferation within organ and thereby organ size (Mizukami, 2001). Recent studies on *Arabidopsis* Aintegumenta (ANT) apparently strengthen this view. ANT seems to function as a coordinator of cell proliferation and lateral organ development. Loss-of-function of ANT reduces the size of leaf and floral organs (Elliott et al., 1996; Klucher et al., 1996; Mizukami and Fischer, 2000), whereas ectopic expression of ANT increases the size of leaf, inflorescence stem and floral organs. These alterations result mainly from changes in total cell number (Krizek, 1999; Mizukami and Fischer, 2000). Further examination reveals that ANT does not affect the growth rate but regulates the extent of organ growth by maintaining the meristematic competence of organ cells, thereby defining intrinsic organ size (Mizukami and Fischer, 2000). At present, the molecular nature of meristematic competence remains unclear (Weigel and Jugens, 2002). In addition, given their sessile and light-dependent life style, organ size in plant is also greatly influenced by environmental and developmental signals, including light, nutrients, and especially plant hormones. Nevertheless, how these signals affect organ development is poorly understood.

The plant hormone auxin plays an essential role in a wide variety of plant growth and developmental process, such as shoot and lateral root formation, apical dominance, tropism and senescence (Davies, 1995). Recent genetic and biochemical analyses have suggested that the ubiquitination-regulated proteolysis is central to several aspects of auxin response (Gray et al., 1999; Gray et al., 2001; Dharmasiri and Estelle, 2002; Kepinski and Leyser, 2002; Leyser, 2002). As a model system, some advances in how auxin promotes lateral root formation have been reported recently (Xie et al., 2000; Casimiro et al., 2001; Xie et al., 2002). However, little is known as to how auxin regulates development of aerial parts of plant. At the cellular level, auxin acts as a signal for cell division, expansion and differentiation (Leyser, 2001), and some lines of evidence at the whole plant level indicate that auxin plays a role in organ cell proliferation as well as organ size (Lincoln et al., 1990; Ecker, 1995). For example, mutation of *Arabidopsis* REVOLUTA (REV)/INTERFASCICULAR FIBERLESS1 (IFL1) prolongs the growth and cell proliferation, resulting in larger leaves, flowers and thicker inflorescent stems (Talbert et al., 1995; Zhong and Ye, 1999). The REV/IFL1 is involved in auxin polar transport, shoot secondary meristem formation and differentiation of interfascicular fibre cell (Zhong and Ye, 2001), suggesting that polar auxin flow may also influence organ development. By contrast, the auxin resistant 1 (axr1) mutant has obviously smaller leaves, inflorescence stems and floral organs, and anatomic examination shows that the reduced size of leaf and stem is caused by a decrease in cell number rather than cell size (Lincoln et al., 1990). Although these observations suggest that AXR1 might be involved in auxin-dependent cell proliferation during development, there is as yet no molecular data to support this claim.

There remains a need in the art, therefore, for a greater understanding of the mechanisms of plant organ development, for methods of regulating this development, and for plants and plant cells in which such development can be regulated.

SUMMARY OF THE INVENTION

The present invention relates to a novel auxin-inducible gene, referred to as ARGOS, that is involved in organ development, including size control, in plants. In an aspect of the invention, over- or reduced-expression of ARGOS in *Arabidopsis* alters the extent of organ growth and cell proliferation, resulting in larger or smaller organs, respectively. In addition, results suggest that ARGOS acts downstream of AXR1 to mediate cell proliferation through ANT during organogenesis.

In particular, the invention provides an isolated nucleic acid which comprises (a) the nucleotide sequence set forth in SEQ ID NO: 1, (b) a nucleotide sequence that encodes the amino acid sequence of SEQ ID NO: 2, or (c) an antisense nucleotide sequence corresponding to a nucleotide sequence of (a) or (b). The present invention also provides vectors comprising the nucleic acid described above, operably linked to a promoter that controls expression in a plant cell. The invention also provides methods of regulating organ development in plants, which include transforming plant cells with the nucleic acids described herein and cultivating the cells into plants.

In particular, the invention provides a method of enhancing organ development in a plant, the method comprising transforming a plant cell with at least one nucleotide sequence operably linked to a promoter, wherein the nucleotide sequence is (a) a nucleic acid comprising the nucleotide sequence set forth in SEQ ID NO: 1 or (b) a nucleic acid comprising a nucleotide sequence that encodes the amino acid sequence of SEQ ID NO: 2, and cultivating the cell into a plant.

The invention also provides a method of inhibiting organ development in a plant, the method comprising transforming a plant cell with at least one nucleotide sequence operably linked to a promoter, wherein the nucleotide sequence is (a) an antisense nucleotide sequence corresponding to the nucleotide sequence set forth in SEQ ID NO: 1, or (b) an antisense nucleotide sequence corresponding to a nucleotide sequence that encodes the amino acid sequence of SEQ ID NO: 2, and cultivating the cell into a plant.

The present invention further provides transformed plant cells and transgenic plants having incorporated into their genomes the nucleic acids described herein, as well as seeds of the described transgenic plants. The present invention additionally provides nucleotide sequences that are homologous to the sequences described herein and which retain the biological activity of the described sequences, as well as methods, transformed cells, transgenic plants, and seeds which use or incorporate these homologous sequences.

BRIEF DESCRIPTION OF THE FIGURES

FIGS. 1A–1H shows the sequences and expression of ARGOS. FIG. 1A: Nucleotide and predicted amino acid sequence of ARGOS (Genbank accession number AY305869; SEQ ID NOs:1–2). FIG. 1B: Induction of ARGOS by auxin. 10 day-old seedlings of Col-O ecotype grown vertically on MS medium were sprayed with 5 µM NAA. Roots and aerial parts were harvested at the time indicated and processed for RNA gel blot analysis. FIG. 1C: Organ specific expression of ARGOS. Inflorescence stems (St), leaves (L), flowers (F) and siliques (Si) were taken from 6 week-old plants grown in a growth chamber. Roots (R) and young rosette leaves (YL) were taken from 2 week-old seedlings grown vertically on MS medium. FIGS. 1D–1F: ARGOS-GUS expression in a 12 day-old seedling (FIG. 1D), flower (FIG. 1E), and young silique (FIG. 1F). Bar=5 mm. FIGS. 1G–1H: Cellular localization of ARGOS-GFP fusion protein (FIG. 1H) and GFP control (FIG. 1G). Bar=100 µm.

FIGS. 2A–2E shows the phenotypic and molecular characterization of ARGOS transgenic plants.

FIGS. 3A–3D shows the anatomical analysis of fifth leaves in transgenic ARGOS plants. FIG. 3A: Adaxial epidermal pavement cells of fully expanded fifth leaves of 35S-anti-ARGOS (left), vector control (middle) and 35S-ARGOS (right) plants. Bar =100 µm. FIG. 3B: Transverse sections of leaf blades of 35S-anti-ARGOS (top), vector control (middle) and 35S-ARGOS (bottom) plants. Bar=100 µm. FIG. 3C: Dimensions of palisade cells. X-, Y- and Z-axis were defined as leaf width, length, and thickness direction, respectively. At least 40 cells of each line were measured under a microscope. Error bars are shown. FIG. 3D: Numbers of palisade cells and total number of mesophyll cells in X-axis and Y-axis of leaves. 4 leaves of each line were sectioned and the cells were counted in the middle of leaves in X-axis and about 1 mm from the midvein in Y-axis. Bar=100 µm. Error bars are shown.

FIGS. 4A–4F shows the effect of ARGOS on growth and cell meristematic competence. FIG. 4A: Eight week-old plant of vector control (left and 35S-ARGOS (fight) grown in a growth chamber. Bar=10 mm. FIG. 4B: Growth kinetics of fifth leaf in 35S-anti-ARGOS, vector control (CK), and 35S-ARGOS plants. 10 leaves from each line were measured afer emergence at an interval of 3 days. Error bars are shown. FIG. 4C: CycB 1-GUS activity in 16 day-old seedling of CK (left) and 35S-ARGOS (fight). Bar=5 mm. FIG. 4D: ANT and CycD3;1 transcfipt levels in juvenile and fully-expanded rosette leaves of vector control (CK) and ARGOS transgenic plants. FIGS. 4E–4F: Neoplasia in leaf explants of ARGOS transgenic plants. FIG. 4E: Note the callus formation in 35S-ARGOS (right) but not in vector control (left). Leaf explants from 4 week-old transgenic plants were cultured on hormone-free MS medium and photographs were taken 10 days after excision. FIG. 4F: Callus growth in leaf explants of vector control (top), 35S-AR GOS (middle) and 35S-anti-ARGOS (bottom) plant. The explants were cultured on MS medium containing 4.5 µM 2,4-D and 0.5 µM kinetin and photographed at 40 days without changing the medium. Bar=5 mm.

FIGS. 5A–5B shows the loss of function of ANT blocks organ enlargement in 35S-ARGOS transgenic plants. FIG. 5A: Morphology of 4 week-old plants (top) and inflorescence (bottom) of 35S-ARGOS/ANTANT or 35S-ARGOS/ANTant-1 (35S-ARGOS/ANT_) and 35S-ARGOS/ant-1ant-1 plants in line L2-4. Bar=10 mm. FIG. 5B:

Endogenous ANT mRNA and transgenic ARGOS mRNA levels in the two types of plants in panel A.

FIGS. 6A–6C shows that ARGOS acts downstream of AXRI.

DETAILED DESCRIPTION OF THE INVENTION

Figure 1:
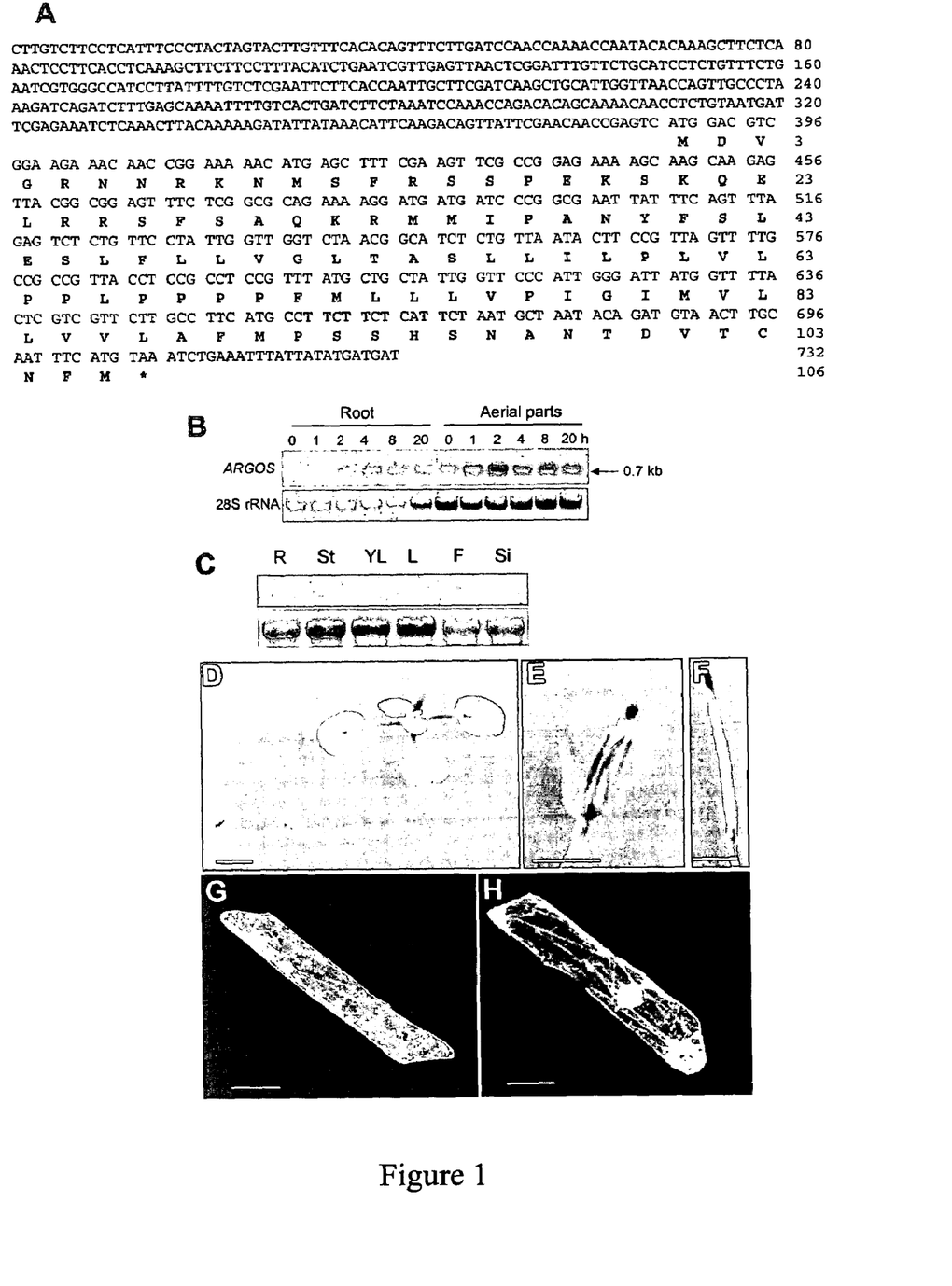

A new auxin-inducible gene involved in plant organ development, Arabidopsis ARGOS, is described. The cloned ARGOS cDNA is 732 bp in length (FIG. 1A) (SEQ ID NO: 1), which is almost full length as analyzed by RNA blot. The putative ARGOS protein (SEQ ID NO: 2) is 106 amino acids in length and contains a leucine-rich domain at the C-terminus (FIG. 1A). ARGOS is distributed in the nucleus as well as the cytosol.

Transgenic plants expressing sense or antisense ARGOS cDNA exhibit enlarged or reduced size of aerial organs, respectively. The alteration in organ size is mainly due to changes in cell number and the duration of organ growth. Ectopic expression of ARGOS prolongs the expression of ANT and CycD3; 1 as well as the neoplastic activity of leaf cells. Moreover, organ enlargement in plants over-expressing ARGOS can be blocked by loss of function of ANT, implying that ARGOS functions upstream of ANT to affect the meristematic competence of organ cells. The induction of ARGOS by auxin is attenuated or abolished in axr1, and over-expression of ARGOS partially restores axr-1 organ development. These results suggest that ARGOS transduces auxin signals downstream of AXR1 to regulate cell proliferation and organ growth through ANT during organogenesis.

An embodiment of the present invention thus provides an isolated nucleic acid which comprises (a) the nucleotide sequence set forth in SEQ ID NO: 1, (b) a nucleotide sequence that encodes the amino acid sequence of SEQ ID NO: 2, or (c) an antisense nucleotide sequence corresponding to a nucleotide sequence of (a) or (b). The nucleic acid may be DNA or RNA, and can be cDNA, genomic DNA, or mRNA. In one embodiment, the nucleic acid is a fusion gene, such as an ARGOS-GUS fusion gene. The present invention also provides a vector comprising the nucleic acid described above, operably linked to a promoter that controls expression in a plant cell. The vector may be a plant expression vector or a vector useful for plant transformation. Any suitable vector well known to skilled artisans may be utilized. An example of a suitable vector is pBI121. The promoter may be any promoter useful for expression of genes in plants. Suitable promoters are well known to skilled artisans, and preferred promoter is the 35S promoter. As is known in the art, promoters can include inducible and/or repressible promoters and enhancers such that the expression of the nucleic acid and encoded polypeptide can be regulated based on various physiological conditions and signals. The nucleic acids of the invention can express the described polypeptides both in vivo and in vitro using various techniques well known to those of skill in the art, including, for example, transduction, transfection or transformation of the nuclaic acid or vector into a cell and in vitro transcription and translation.

The invention further provides a method of enhancing organ development in a plant, the method comprising transforming a plant cell with at least one nucleotide sequence operably linked to a promoter, wherein the nucleotide sequence is (a) a nucleic acid comprising the nucleotide sequence set forth in SEQ ID NO: 1 or (b) a nucleic acid comprising a nucleotide sequence that encodes the amino acid sequence of SEQ ID NO: 2, and cultivating the cell into a plant. Cultivating the cell into a plant can involve any technique, including those described herein and others known in the art, for growing or continuing to grow a plant cell to a mature plant. The promoter may be any suitable promoter and is preferably a 35S promoter. The plant may be any plant species. Examples of plant species include tobacco, vegetables, flowers, herbs and Arabidopsis thaliana, e.g., Arabidopsis thaliana Columbia.

In the methods described herein, the organ is any plant organ, but preferably a lateral organ, such as a leaf. In an embodiment, the leaf is a rosette leaf. The organ may also be a floral organ, an inflorescence stem, or a silique. Organ development encompasses all aspects of the developmental control of morphogenesis, including the coordination of cell growth, cell division and cell differentiation and the reflection of this coordination as seen in organ growth and resulting overall plant growth. The sequences of the present invention can be introduced into any plant of interest using techniques well known to skilled artisans, and can be used to transform any plant species using techniques will known to skilled artisans. The sequences to be introduced can be contained in expression cassettes for expression in the particular plant of interest. Examples of plant species include tobacco, vegetables, flowers, herbs and Arabidopsis thaliana, e.g., Arabidopsis thaliana Columbia.

In a preferred embodiment, the enhanced development is an increase in organ growth. In further preferred embodiments of the invention, organ development is enhanced by about 50% to about 120%. The enhanced development may also be manifested in a longer hypocotyl in a de-etiolated seedling of the plant. The enhanced development can include delayed flowering or an increase in seed number in a silique of the plant. The increase in seed number can be about 20%. The enhanced organ growth can be a result of increased cell number. The increase can be about 30%. In an embodiment, the enhanced development is an extension of growth duration. This extension can be due to extended cell proliferation.

The invention further provides a method of inhibiting organ development in a plant, the method comprising transforming a plant cell with at least one nucleotide sequence operably linked to a promoter, wherein the nucleotide sequence is (a) an antisense nucleotide sequence corresponding to the nucleotide sequence set forth in SEQ ID NO: 1, or (b) an antisense nucleotide sequence corresponding to a nucleotide sequence that encodes the amino acid sequence of SEQ ID NO: 2, and cultivating the cell into a plant. The promoter may be any suitable promoter and is preferably a 35S promoter. The plant may be any plant species. Examples of plant species include tobacco, vegetables, flowers, herbs and Arabidopsis thaliana, e.g., Arabidopsis thaliana Columbia.

In a preferred embodiment, the inhibited organ development is a decrease in organ growth. In preferred embodiments, the growth can be decreased by about 20% to about 60%. The inhibited development can be manifested in a shorter hypocotyl in a de-etiolated seedling of the plant. The inhibited development can also include earlier flowering or a decrease in seed number in a silique of the plant. The inhibited organ growth can be a result of decreased cell number in the organ and the decrease can be about 20%. The inhibited development can also be a decrease in growth duration.

The present invention also provides a transformed plant cell having stably incorporated into its genome at least one nucleotide sequence operably linked to a promoter, wherein the nucleotide sequence is (a) a nucleic acid comprising the nucleotide sequence set forth in SEQ ID NO: 1, (b) a nucleic acid comprising a nucleotide sequence that encodes the amino acid sequence of SEQ ID NO: 2, or (c) a nucleic acid comprising an antisense nucleotide sequence corresponding to a nucleotide sequence of (a) or (b). The promoter can be any suitable promoter and is preferably a 35S promoter. The cell can be of any plant type and any species. Examples of plant species include tobacco, vegetables, flowers, herbs and *Arabidopsis thaliana*, e.g., *Arabidopsis thaliana* Columbia.

The present invention further provides a transgenic plant having stably incorporated into its genome at least one nucleotide sequence operably linked to a promoter, wherein the nucleotide sequence is (a) a nucleic acid having the nucleotide sequence set forth in SEQ ID NO: 1, (b) a nucleic acid having a nucleotide sequence that encodes the amino acid sequence of SEQ ID NO: 2, or (c) a nucleic acid having an antisense nucleotide sequence corresponding to a nucleotide sequence of (a) or (b). The promoter can be any suitable promoter and is preferably a 35S promoter. The plant can be any plant species. Examples of plant species include tobacco, vegetables, flowers, herbs and *Arabidopsis thaliana*, e.g., *Arabidopsis thaliana* Columbia. The invention also provides seeds of the transgenic plants described herein.

The invention further provides a method of regulating organ development in a plant, the method comprising transforming a plant cell with at least one nucleotide sequence operably linked to a promoter, wherein the nucleotide sequence is (a) a nucleic acid comprising the nucleotide sequence set forth in SEQ ID NO: 1, (b) a nucleic acid comprising a nucleotide sequence that encodes the amino acid sequence of SEQ ID NO: 2, or (c) a nucleic acid comprising an antisense nucleotide sequence corresponding to a nucleotide sequence of (a) or (b) and cultivating the cell into a plant. The promoter can be any suitable promoter and is preferably a 35S promoter. The plant can be any plant species. Examples of plant species include tobacco, vegetables, flowers, herbs and *Arabidopsis thaliana*, e.g., *Arabidopsis thaliana* Columbia.

In a preferred embodiment, the organ development is organ growth. The regulated organ growth may be a result of altered cell division or altered cell number. In another embodiment, the organ development is organ cell proliferation.

The present invention further provides a nucleotide sequence having greater than 50% homology to a full-length nucleotide sequence set forth in SEQ ID NO: 1, wherein the homologous nucleotide sequence encodes a polypeptide which retains the biological activity of the full length sequence, namely, the regulating organ development activities described herein. The homology of the nucleotide sequence is preferably about 80%, and more preferably, about 95%.

The invention further provides a method of enhancing organ development in a plant, comprising transforming a plant cell with at least one nucleotide sequence operably linked to a promoter, wherein the nucleotide sequence is (a) a nucleotide sequence having greater than 50% homology to a full-length nucleotide sequence set forth in SEQ ID NO: 1, wherein said homologous nucleotide sequence encodes a polypeptide which retains biological activity of the full length sequence or (b) a nucleotide sequence having greater than 50% homology to a nucleotide sequence that encodes the amino acid sequence of SEQ ID NO: 2, wherein said nucleotide sequence encodes a polypeptide which retains biological activity of the full length sequence, and cultivating the cell into a plant. The homology of the nucleotide sequence is preferably about 80%, and more preferably, about 95%.

The invention further provides a method of inhibiting organ development in a plant, comprising transforming a plant cell with at least one nucleotide sequence operably linked to a promoter, wherein the nucleotide sequence is (a) an antisense nucleotide sequence corresponding to a nucleotide sequence having greater than 50% homology to the nucleotide sequence set forth in SEQ ID NO: 1 or (b) an antisense nucleotide sequence corresponding to a nucleotide sequence having greater than 50% homology to a nucleotide sequence that encodes the amino acid sequence of SEQ ID NO: 2, and cultivating the cell into a plant. The homology of the nucleotide sequence is preferably about 80%, and more preferably, about 95%.

The present invention further provides a transformed plant cell having stably incorporated into its genome at least one nucleotide sequence operably linked to a promoter, wherein the nucleotide sequence is (a) a nucleotide sequence having greater than 50% homology to a full-length nucleotide sequence set forth in SEQ ID NO: 1, wherein said homologous nucleotide sequence encodes a polypeptide which retains biological activity of the full length sequence, (b) a nucleotide sequence having greater than 50% homology to a nucleotide sequence that encodes the amino acid sequence of SEQ ID NO: 2, wherein said nucleotide sequence encodes a polypeptide which retains biological activity of the full length sequence, or (c) an antisense nucleotide sequence corresponding to a nucleotide sequence of (a) or (b). The homology of the nucleotide sequence is preferably about 80%, and more preferably, about 95%.

The present invention further provides a transgenic plant having stably incorporated into its genome at least one nucleotide sequence operably linked to a promoter, wherein the nucleotide sequence is (a) a nucleotide sequence having greater than 50% homology to a full-length nucleotide sequence set forth in SEQ ID NO: 1, wherein said homologous nucleotide sequence encodes a polypeptide which retains the biological activity of the full length sequence, (b) a nucleotide sequence having greater than 50% homology to a nucleotide sequence that encodes the amino acid sequence of SEQ ID NO: 2, wherein said nucleotide sequence encodes a polypeptide which retains the biological activity of the full length sequence, or (c) an antisense nucleotide sequence corresponding to a nucleotide sequence of (a) or (b). The homology of the nucleotide sequence is preferably about 80%, and more preferably, about 95%. The invention also provides a seed of this transgenic plant.

As used herein, an isolated or purified nucleic acid or protein, or biologically active portion thereof, is substantially free of other cellular material, or culture medium when produced by recombinant techniques, or substantially free of chemical precursors or other chemicals when chemically synthesized. Preferably, an isolated nucleic acid is free of sequences (preferably protein encoding sequences) that naturally flank the nucleic acid (i.e. sequences located at the 5' and 3' ends of the nucleic acid) in the genomic DNA of the organism from which the nucleic acid is derived.

The polynucleotide or nucleic acid compositions of the present invention include RNA, cDNA, genomic DNA, synthetic forms, and mixed polymers, both sense and anti-sense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides of the invention may be isolated or substantially pure.

Recombinant constructs comprising the ARGOS gene may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are additionally provided by this invention. Although the described sequences may be employed, they will often be altered, e.g., by deletion, substitution or insertion.

Protein modifications or fragments are provided by the present invention for wildtype and mutant ARGOS polypeptides or fragments thereof which are substantially homologous to primary structural sequence but which include, for example, in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by persons of ordinary skill in the art. A variety of methods for labeling polypeptides and a variety of substituents or labels useful for such purposes are well known by persons of ordinary skill in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation.

As described, in addition to substantially full-length proteins, the present invention provides for biologically active fragments and homologs of the polypeptides. The term "polypeptide" as used herein refers to both a full length protein and a portion of the protein as a polypeptide fragment.

The present invention also provides for fusion polypeptides, comprising ARGOS polypeptides and fragments thereof and polypeptides or fragments of other proteins as known in the art. Homologous polypeptides may be fusions between two or more polypeptide sequences or between the sequences of ARGOS and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as immunoglobulins, bacterial β-galactosidase, trpE, protein A, β-lactamase, alpha amylase, alcohol dehydrogenase and yeast alpha mating factor.

Fusion proteins will typically be made by either recombinant nucleic acid methods, as described below, or may be chemically synthesized. Techniques for the synthesis of polypeptides are well known by persons of ordinary skill in the art.

Other protein modifications include amino acid substitution. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; asp artic acid, glutamic acid; asparagine, glutamine; serine, threonine; lysine, arginine; and tyro sine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art. Alternatively, the substitution of like amino acids can be made effectively on the basis of hydrophilicity. The importance of hydrophilicity in conferring interactive biological function of a protein is generally understood in the art (See e.g. U.S. Pat. No. 4,554,101). The use of the hydrophobic index or hydrophilicity in designing polypeptides is further discussed in U.S. Pat. No. 5,691,198.

A recombinant nucleic acid is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. This phrase is also meant to encompass a gene which is removed from its normal regulatory expression constraints, as in the case where a gene product is overexpressed due to the presence of multiple copies of the gene or up regulated promoter or enhancer signals, increased mRNA or protein half life and the like.

"Regulatory sequences" refers to those sequences which affect the expression of the gene (including transcription of the gene, and translation, splicing, stability or the like of the messenger RNA).

Large amounts of the polynucleotides of the present invention may be produced by a suitable host cell transformed with a nucleotide sequence described herein. Natural or synthetic polynucleotide fragments coding for the peptide or a desired fragment can be incorporated into recombinant polynucleotide constructs (vectors), usually DNA constructs, capable of introduction into and replication in a prokaryotic or eukaryotic cell. Typically, the vectors will be suitable for replication in a unicellular host, such as yeast or bacteria, but may also be intended for introduction to (with and without integration within the genome) cultured mammalian or plant or other eukaryotic cell lines. The most commonly used prokaryotic hosts are strains of *Escherichia coli*, although other prokaryotes, such as *Bacillus subtilis* or *Pseudomonas* may also be used. Mammalian or other eukaryotic host cells, such as those of yeast, filamentous fungi, plant, insect, or amphibian or avian species, may also be useful for production of the proteins of the present invention. As is well known in the relevant art, regulating polynucleotide expression can result in regulation of polypeptides encoded by the polynucleotide.

Expression and cloning vectors preferably contain a selectable marker gene. Typical marker genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of an appropriate selectable marker will depend on the host cell, and appropriate markers for different hosts are well known to persons of ordinary skill in the art.

The vectors containing the nucleic acids of interest can be transcribed in vitro, and the resulting RNA introduced into the host cell by well-known methods, e.g., by injection, or the vectors can be introduced directly into host cells by methods well known to persons of ordinary skill in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Clones are selected by using markers, depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention are useful not only for the production of the nucleic acids and polypeptides of the present invention, but also, for example, in studying the characteristics of ARGOS polypeptides. Plant cells transformed with the polynucleotoides of the present invention are useful also for growing plants expressing the polynucleotides and polypeptides of the present invention. The nucleotides of the present invention can also be transformed into plants that have already undergone some growth.

A polynucleotide of the present invention can be expressed in either sense or antisense orientation, as desired. It will be appreciated that control of gene expression in either sense or antisense orientation can have a direct impact on the observable plant characteristics. Antisense technology, known in the art, can be conveniently used for gene expression in plants. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest.

In light of the preceding description, one of ordinary skill in the art can practice the invention to its fullest extent. The following examples, therefore, are merely illustrative and should not be construed to limit in any way the invention as set forth in the claims which follow.

EXAMPLE 1

Methods

Plant Materials and Growth Conditions: *Arabidopsis* Columbia (Col.) ecotype was used. Seeds were sterilized in 50% bleach with 0.1% Triton X-100 for 10 min. and washed three times with sterilized water. Sterilized seeds were plated on MS medium, and vernalized in darkness at 4° C. for 2 days before the plates were transferred to a culture room at 23° C. under a 16 h-light/8 h-dark photoperiod. For NAA treatment or root observation, seeds were germinated and seedlings were grown vertically for 7–14 days. For morphological examination of aerial parts, seedlings were transferred to soil 7–10 days after germination, and placed in a growth chamber at 23° C. under a 16 h-light/8 h-dark photoperiod.

Plant Transformation: A cDNA fragment containing the ARGOS ORF was cloned into pVIP96 (Leu et al., 1995) in sense and antisense orientation. Transgenic plants were generated by *Agrobacterium tumefaciens*-mediated transformation via vacuum infiltration (Betchtold et al., 1993). T1 seeds and progenies were germinated on MS medium containing 50 mg/L kanamycin for the selection of transformats. At least 2 independent T3 homozygous lines with a single T-DNA insertion were used for detailed analysis.

Gene Expression Analysis: Total RNA was isolated using the guanidine thiocyanate extraction buffer as described (Hu et al., 2000), and each gel lane contained about 10 μg total RNA. RNA gel blots were probed with ARGOS cDNA fragment labeled by $\alpha$-$^{32}$PdCTP using a Ready Primer Labeling Kit (Amersham). To identify expression of the ARGOS sense transgene, ARGOS RNA complementary probe was synthesized by T3 RNA polymerase (Promega) and labeled with a $\alpha$-$^{32}$PUTP. The endogenous ARGOS expression in transgenic plants was detected using as a probe a 250 bp fragment from the ARGOS 5'-nontranslated region. Hybridizations were performed as described previously (Church and Gilbert, 1984). RT-PCR was carried out with QIAGENE one-step RT-PCR kit.

A 2.1 kb DNA fragment containing the 5' upstream region of ARGOS was cloned into pBI101 for construction of the ARGOS-GUS fusion gene. The SalI-BamHI fragment containing CycB1; 1-GUS (Ferreira et al., 1994) was cloned into pCambia1300, and transformed into plants carrying 35S-ARGOS and empty vector for examination of cell proliferation in leaf development. To monitor GUS expression, seedlings or young organs of transgenic plants were incubated in a 50 mM Na-phosphate (PH7.0) solution containing 5 mM $K_4Fe(CN)_6$, 5 mM $K_3Fe(CN)_6$, 0.1% Triton X-100 and 1 mM X-Gluc at 37° C. for several hours.

To determine the cellular localization of ARGOS, an ARGOS coding region was fused in frame upstream or downstream of the GFP coding sequence in the vector pGFP2 or pGFP2 (5 GA) II (Kost et al., 1998), which contain a 35S-GFP gene. After bombardment, onion peels were kept in darkness for 6–12 hours, and GFP expression was visualized under a confocal microscopy.

Histological Analysis: Fully expended fifth leaves and flower organs were cryofixed in liquid nitrogen and scanned with a scanning electron microscope (SEM) for the examination of epidermal cell. To determine cell size and number in thin section, specimens of fully expanded fifth leaf (35 days after germination) and the second internode of inflorescence stem were fixed in 100 mM K-phosphate buffer (PH7.2) containing 2.5% glutaraldehyde. After dehydration with an ethanol series, samples were infiltrated and embedded with Leica Historesin Embedding Kit according to the manufacturer's instructions. Cell size was measured and cell number was determined in middle region of the fifth leaf blade in transverse section or about 1 mm beside midvein in longitudinal section.

Leaf Explant Culture: To test leaf cell competency, rosette leaves of 4 week-old control and ARGOS transgenic plants were sterilized and excised. The explants were cultured on a hormone-free MS medium and a callus induction medium, under a 16 h-light/8 h-dark photoperiod at 23° C. The callus induction medium used is MS medium containing 4.5 µM 2,4-dichlorophenoxyacetic acid (2,4-D) and 0.5 µM kinetin (Hu et al., 2000).

EXAMPLE 2

ARGOS is a Novel Gene and Highly Induced by Auxin

Previous studies showed that the *Arabidopsis* NAC1 and SINAT5 mediate auxin signals to promote lateral root development (Xie et al., 2000; Xie et al., 2002). To further understand the molecular events surrounding auxin-regulated lateral root formation, a cDNA microarray analysis was performed by Incyte Genomics to identify genes responsive to NAA treatment in roots of 7 day-old seedlings (unpublished data). One gene, which is identical to the putative gene At3g59900 in *Arabidopsis* database, was found to be highly induced by NAA treatment (data not shown). We designated this gene as ARGOS (for Auxin-Regulated Gene involved in Organ Size, see below). RNA gel blot analysis showed that the expression of ARGOS was induced by auxin in both roots and aerial parts (FIG. 1B).

The cloned ARGOS cDNA is 732 bp in length (FIG. 1A)(SEQ ID NO: 1), which is almost full length as analyzed by RNA blot. The putative ARGOS protein (SEQ ID NO: 2) is 106 amino acid in length and contains a leucine-rich domain at the C-terminus (FIG. 1A). Blast search in GenBank showed that except for a putative homolog found in the rice genome, no other homolog has been identified, indicating that ARGOS is a novel protein and possibly plant specific. The *Arabidopsis* genome contains another putative gene that displays about 50% identity to ARGOS, but its organ-specific expression pattern and response to auxin are different from those of ARGOS (unpublished data). Moreover, high stringency Southern blot analysis using a DNA probe prepared from the ARGOS open reading frame indicated that ARGOS is a single copy gene (data not shown).

EXAMPLE 3

Expression and Cellular Localization of ARGOS

To determine the expression pattern of ARGOS, RNAs from the dissected organs of mature plant as well as rosette leaves of two-week old seedlings were analyzed. ARGOS was expressed at low levels in roots, inflorescence stems, flowers, young rosette leaves and siliques (FIG. 1C). A detailed examination was performed with transgenic plants expressing an ARGOS-GUS fusion gene. In 12 day-old seedlings, strong GUS expression was observed in root pericycle, petiole and leaf vascular bundles, and moderate GUS expression was detected in leaf blade (FIG. 1D). In flowers, high expression levels were seen in stamen filaments as well as in the apex and base of juvenile and elongating siliques (FIGS. 1E, F).

Computer programs predicted the C-terminal leucine-rich domain of ARGOS to be a putative transmembrane domain. We therefore investigated its cellular localization in onion epidermal cells using 35S-ARGOS-GFP and 35S-GFP-ARGOS fusion genes. GFP fluorescence was observed in the nucleus, cytoplasm and cytoplasmic membrane of cells, similar to that obtained with vector control (FIGS. 1G-H). These results indicate that ARGOS is distributed in the nucleus as well as the cytosol.

EXAMPLE 4

Alteration of ARGOS Expression Affects Lateral Organ Size

Figure 2:
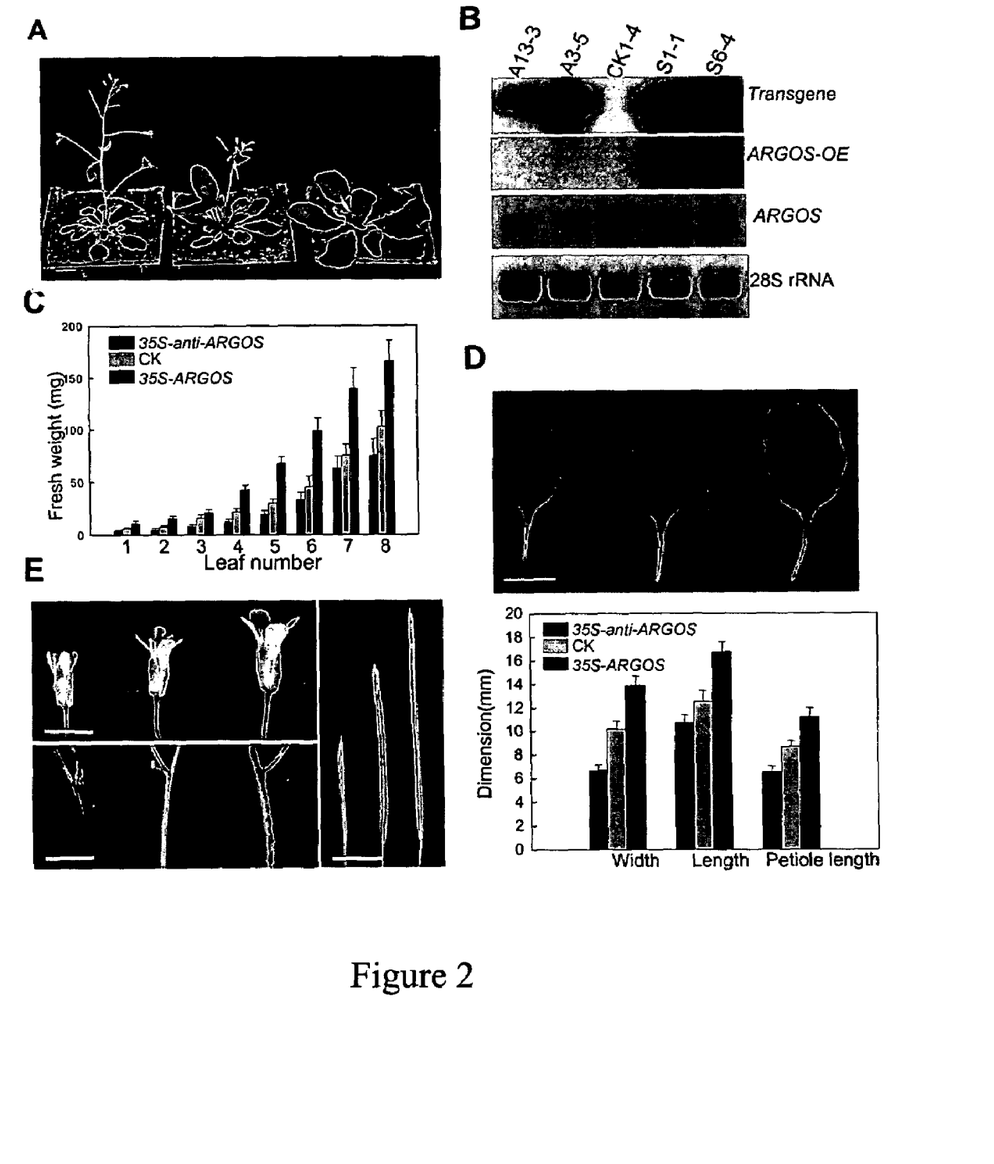
FIG. 2A: 30 day-old plants of 35S-anti-ARGOS (left), vector control (middle) and 35S-ARGOS (right) grown in a growth chamber at 23° C. under a 16h-light/8h-dark photoperiod. Bar=10 mm.
FIG. 2B: Expression analyses of ARGOS in transgenic plants. A vector control line (CK1-4) and two independent lines of 35-anti-ARGOS (A3-5,A13-3) and 35S-ARGOS (S1-1, S6-4) were used to analyze transgenic and endogenous gene expression. The RNA gel blot was probed with ARGOS coding region for transgene expression, with an anti-ARGOS RNA to detect over-expression of ARGOS (ARGOS-OE) and with a 5'-nontranslated region of ARGOS for endogenous ARGOS expression (ARGOS).
FIG. 2C: Leaf fresh weight of 6 week-old plants. At least 10 plants from two independent lines were measured in vector control, 35S-anti-ARGOS and 35S-ARGOS plants. N=10 and error bars are shown.
FIG. 2D: Morphology (top panel) and dimensions (bottom panel) of 5 week-old fifth leaves. Bar=5 mm. N=10 and error bars are shown.
FIG. 2E: Phenotype of flower, inflorescence stem and silique of 35S-anti-ARGOS, vector control, and 35S-ARGOS plants (from left to right). Bar=5 mm.

To investigate the function of ARGOS during plant growth and development, transgenic 35S-ARGOS and 35S-anti-ARGOS plants were generated. Among the 20 lines analyzed in each construct, 12 sense lines and 5 antisense lines showed an enlarged or reduced leaf size, respectively, in comparison to empty vector control lines (FIG. 2A). RNA gel blot analyses performed with two independent lines with a single insertion confirmed the over-expression of ARGOS RNA in the sense plants and the decreased mRNA level of endogenous ARGOS in the antisense plants (FIG. 2B).

ARGOS sense and antisense plants differed significantly in their leaf size. Compared to vector control plants, the fresh weight of the corresponding leaf in ARGOS sense lines increased 50–120%, whereas, that in the ARGOS antisense plants decreased 20-60% (FIG. 2C). The fifth rosette leaf was chosen for further phenotypic analyses, as it was found to be most representative in *Arabidopsis* (Tsuge et al., 1996; Tsukaya, 2002). Detailed examination showed that the blade width, length, and petiole length of the fifth leaf were greatly increased or decreased in ARGOS sense or antisense plants, respectively (FIG. 2D). Similar changes were also observed in floral organs, inflorescence stems and siliques of ARGOS transgenic plants (FIG. 2E). A corresponding increased or decreased plant height was also found in ARGOS transgenic plants (Table 1).

TABLE 1

Morphology of ARGOS Transgenic Plants

|  | 35S-anti-ARGOS | Vector Control | 35S-ARGOS |
|---|---|---|---|
| Cytoledon width (mm) | 3.50 ± 0.32 (n = 6) | 3.42 ± 0.37 (n = 6) | 3.56 ± 0.38 (n = 12) |
| length (mm) | 6.50 ± 0.55 | 7.33 ± 0.61 | 5.58 ± 0.38 |
| Hypocotyl length[a] (mm) | 12.6 ± 2.2 (n = 22) | 14.6 ± 1.7 (n = 29) | 17.4 ± 3.1 (n = 33) |
| Flowering time (d) | 23.1 ± 1.8 (n = 15) | 26.6 ± 2.3 (n = 15) | 33.8 ± 1.7 (n = 15) |
| Silique length (mm) | 7.46 ± 0.75 (n = 20) | 13.0 ± 1.04 (n = 20) | 16.92 ± 1.07 (n = 20) |
| Seeds/silique | 31.5 ± 6.7 | 55.6 ± 2.54 | 67.4 ± 5.1 |
| Plant height (cm) | 33.7 ± 3.31 (n = 5) | 44.3 ± 1.94 (n = 5) | 57.3 ± 1.25 (n = 5) |

[a]Seedlings grown in darkness for 5 days.

Transgenic plants over- or under-expressing ARGOS also displayed other notable alterations during development. Compared to vector control plants, longer and shorter hypocotyls were found in de-etiolated seedlings of sense or antisense lines, respectively (Table 1). Furthermore, flowering in transgenic plants over-expressing ARGOS was delayed by about one week and these plants produced 20% more seeds in each silique compared to vector control plants. By contrast, ARGOS antisense plants flowered earlier and their siliques contained fewer seeds at maturity (Table 1). These observations indicate that alteration of ARGOS expression in plants greatly affect lateral organ growth and development.

EXAMPLE 5

Figure 3:
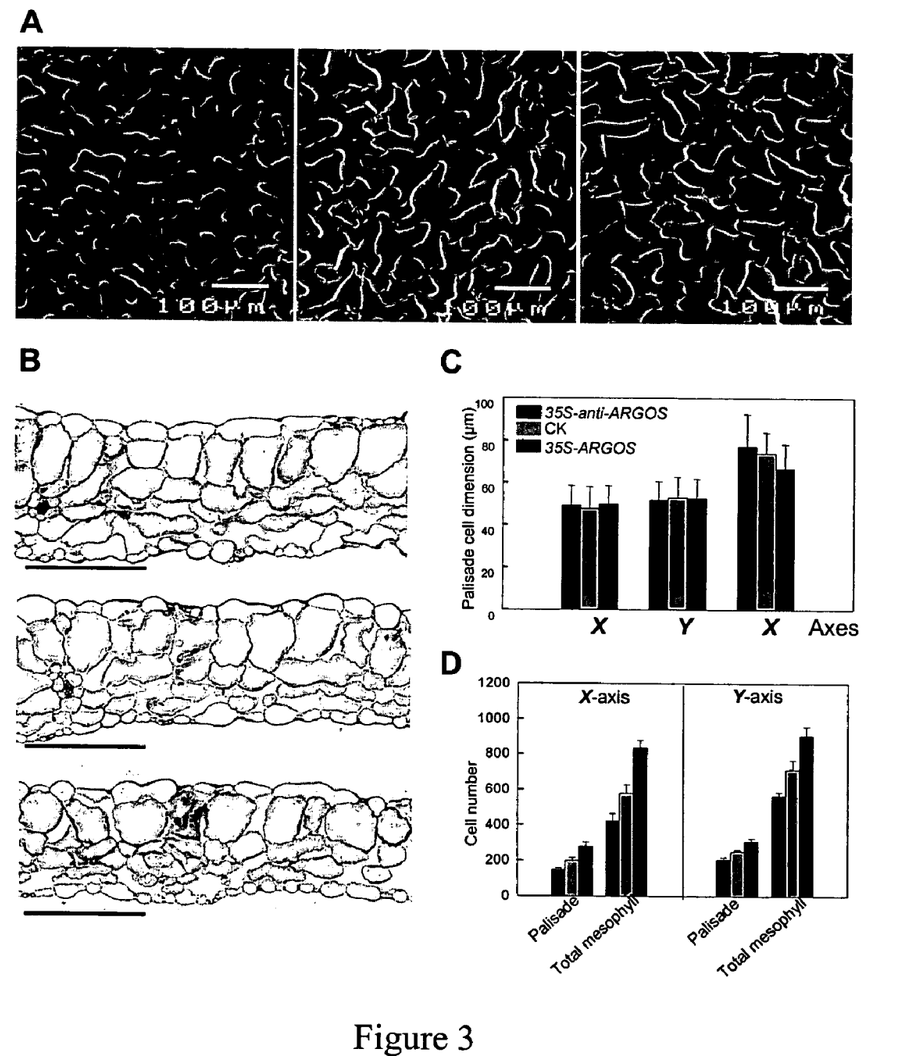

Changes of Organ Size in ARGOS Transgenic Plants are Mainly Due to Changes in Cell Number To assess the contributions of cell division and cell expansion to the phenotypes of ARGOS transgenic plants, adaxial epidermal pavement cells of fully expanded fifth leaf were visualized with scanning electron microscope (SEM). Although the pavement cells are jigsaw-puzzle-like and variable in size in *Arabidopsis* (Van Lijsebettens and Clarke, 1998), comparison of epidermal pavement cells among vector control and ARGOS transgenic plants revealed an almost equal size between vector control and ARGOS sense plants, but slightly larger in antisense plants (FIG. 3A). This suggests that cell size is not responsible for altered leaf size.

Transverse and longitudinal sections of leaf blade were then analyzed. Leaf blades from three groups of plants appeared to contain the same number of cell layers (FIG. 3B). For characterization of leaf cells, we defined X-, Y- and Z-axis as leaf width, length and thickness direction, respectively. As shown in FIGS. 3B and 3C, the dimensions of palisade cells from three groups of plants varied slightly in three axes, and a decreased dimension of palisade cells in Z-axis was observed in ARGOS over-expressing leaves. However, the number of palisade cells and the total number of mesophyll cells in both X- and Y-axis differed significantly. The leaf blade of 35S-ARGOS plants contained about 30% more cells than that of vector control plants, whereas that of 35S-anti-ARGOS plants contained about 20% fewer cells (FIG. 3D). These results suggest that cell number contributes to the enlarged or reduced organ size in ARGOS transgenic plants. To further confirm this observation, we examined inflorescence stems in thin sections and floral organs by SEM. No striking differences in cell size were observed among these three lines except that the size of petal epidermal cells in 35S-ARGOS sense plants appeared to be larger than those in vector control and antisense lines. However, the slightly larger cell size could not account for the enlarged petal size (data not shown). Therefore, we concluded that the altered organ size in ARGOS transgenic plants results mainly from changes in cell number.

EXAMPLE 6

Expression of ARGOS Affects Duration of Plant Growth and Cell Proliferation

Figure 4:
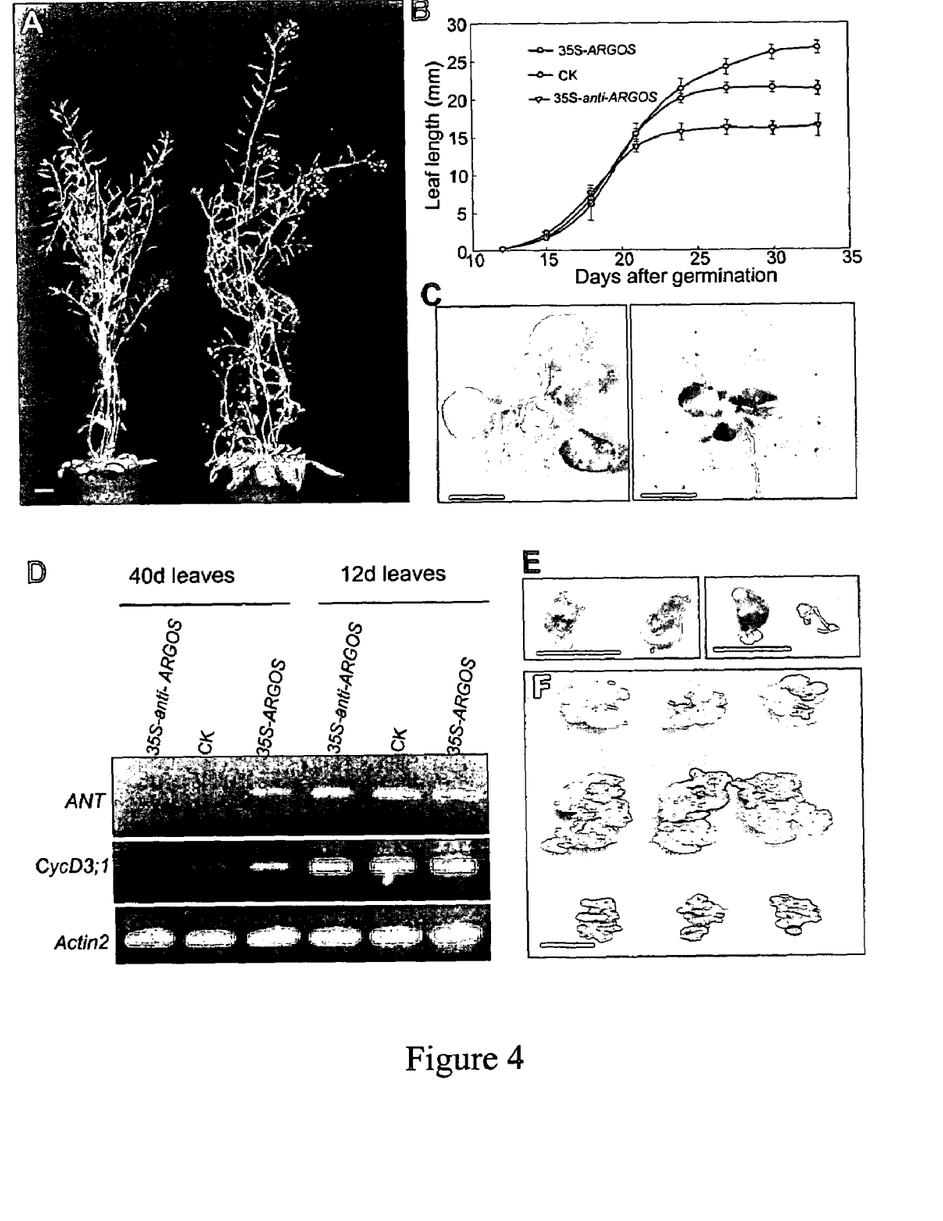

Visible difference in the first rosette leaf appeared about 10 days after germination in seedlings of vector control and transgenic lines. Eight week-old plants of vector control stopped flowering in most of the inflorescences, and their leaves began to senesce (FIG. 4A). By contrast, 35S-ARGOS plants continued to flower in almost all inflorescences and their leaves remained dark-green (FIG. 4A), suggesting that ectopic expression of ARGOS extends the period of growth. To confirm this, we further investigated the growth kinetics of fifth rosette leaves. Under our growth condition, the fifth rosette leaf emerged at about 11 days after germination. The total leaf length of vector control and ARGOS transgenic plants increased similarly in the following 12 days. Leaves of antisense plants ceased elongation at about 24 days after germination, followed by that of control at 27 days. However, 35S-ARGOS leaves continued to grow even after 33 days (FIG. 4B). These data demonstrate that variations in the growth duration, rather than the growth rate, contribute to the differences in organ size in ARGOS transgenic plants.

To determine the role of cell division in altered duration of leaf development, we introduced a CycB1-GUS transgene into vector control and 35S-ARGOS plants. CycB1 is expressed at the G2/M phase of the cell cycle, and CycB1-GUS has been used as a marker for studies of cell proliferation in lateral organ development (Ferreira et al., 1994; Donnelly et al., 1999; Casimiro et al., 2001). At 16 days after germination, GUS staining in transgenic vector control seedling was observed in leaf primordia and marginal meristems of young leaves, but less marginal and diffused sub-marginal cell division occurred in expanding leaves (FIG. 4C). By contrast, 35S-ARGOS seedlings displayed prolonged cell division in marginal meristems as well as in leaf blade, giving more visible marginal meristems and more diffused cell division in expanding leaves (FIG. 4C). Besides cell expansion, lateral growth of leaf was thought to depend on marginal and sub-marginal cell proliferation within the leaf blade (Donnelly, et al., 1999). Thus, our observation suggests that ectopic expression of ARGOS extends the period of cell proliferation in organs.

EXAMPLE 7

ARGOS Influences ANT Expression and Cell Competence

To test whether ARGOS affects organ cell competence, thus influencing the duration of cell proliferation, we analyzed the expression of ANT and CycD3;1 in fully expended and young rosette leaves of vector control and ARGOS transgenic plants. Compared to the undetectable expression in vector control and ARGOS anti-sense leaves, the expression of ANT persisted in rosette leaves of 40-day old 35S-ARGOS plants (FIG. 4D). Meanwhile, similar to that in 35S-ANT plants (Mizukami and Fischer, 2000), prolonged expression of CycD3;1 was also detected in 35S-ARGOS leaves (FIG. 4D). These results suggest that the ectopic expression of ARGOS extends the expression of ANT as well as cell division genes. In addition, an increased or decreased ANT transcript was detected in 10-day old rosette leaves of 35S-ARGOS sense or antisense seedlings, respectively. However, comparable levels of CycD3;1 transcripts were observed in those of vector control and ARGOS transgenic seedlings (FIG. 4D). This is consistent with the previous finding that ectopic expression of ANT does not increase CycD3;1 expression in tissues in which most cells are meristematic (Mizukami and Fischer, 2000).

Neoplasia was observed in 35S-ARGOS leaf cells. When cultured on hormone-free MS media, 35S-ARGOS leaf plants but not explants from vector control or antisense plants generated small calli after one week (FIG. 4E). Moreover, striking differences were seen when the leaf explants were cultured on a callus induction medium for a longer time period without being transferred to fresh medium. All explants produced calli in one week, but ARGOS antisense calli ceased to grow at about 20 days, as did the control at about 30 days. By contrast, calli of 35S-ARGOS sense continued to grow even after 40 days (FIG. 4E). These results suggest that over- or under-expression of ARGOS affects cell competence.

EXAMPLE 8

ARGOS Mediates Organ Growth Upstream of ANT

Figure 5:
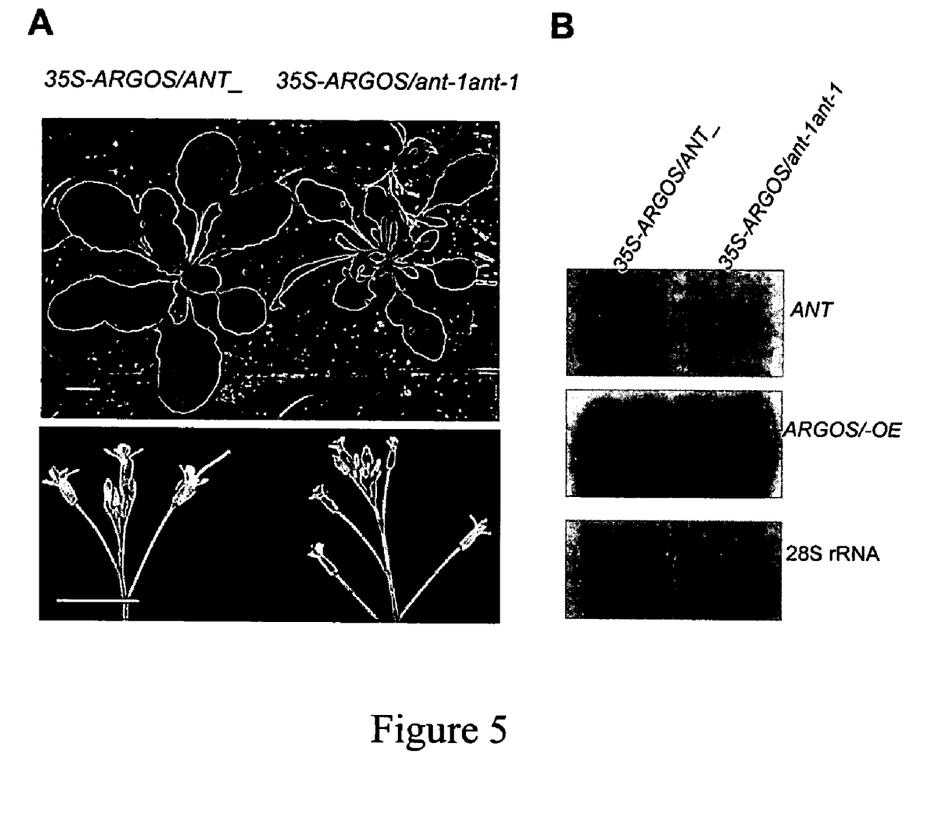

The prolonged expression of ANT and altered cell competence in 35S-ARGOS transgenic plants implies that ARGOS may function through regulation of ANT expression. To address this, we crossed homozygous 35S-ARGOS transgenic plants with ANT/ant-1, and analyzed F2 progeny. Among 121 35S-ARGOS plants from two independently segregating lines, 86 displayed enlarged leaves and floral organs of 35S-ARGOS plants; however, 35 exhibited ant-i phenotype with small leaves and floral organs (FIG. 5A). These results are consistent with the expected genetic segregation ratios. RNA gel blot analyses showed that these two types of plants expressed comparable high levels of ARGOS-OE (FIG. 5B). These results indicate that loss of function of ANT can block ARGOS-mediated organ growth and hence ARGOS functions upstream of ANT.

EXAMPLE 9

Induction of ARGOS by Auxin is Attenuated or Abolished in axr1 Mutants

A number of mutants involved in auxin transport and signaling have been identified, but only the axr1 mutant was reported to have smaller leaf and shorter inflorescence stems resulting from decreased cell numbers (Lincoln et al., 1990). To investigate whether ARGOS is involved in AXR1-related control of organ development, we examined ARGOS expression in seedlings treated with/without NAA in axr1–3 and axr1–12 as well as some auxin-related mutants. Compared to WT, the apparently decreased levels of ARGOS expression were observed in axr1–3 and axr1–12, and the induction of ARGOS by NAA treatment was strikingly attenuated in axr1–3 and completely abolished in axr1–12 (FIG. 6A). However, ARGOS induction by NAA treatment was still observed in axr2, tir1–3, aux1–7 and iaa28 (data not shown). These results, together with the observation that defects in organ development in axr1–12 are more severe than that in axr1–3 (Lincoln et al., 1990), suggest that ARGOS is involved in AXR1-mediated auxin signaling.

EXAMPLE 10

Over-expression of ARGOS Partially Restores the Organ Development in axr1

To further investigate the role of ARGOS in auxin signaling mediated by AXR1, 35S-ARGOS were introduced into axr1–3. Although the morphology of leaves in transgenic 35S-ARGOS/axr1–3 plants were similar to that in axr1–3, over-expression of ARGOS apparently restored a part of the axr1–3 leaf development, producing similar sized leaves of or even larger leaves compared to WT leaves (FIG. 6B). As a negative control, we found that transgenic axr1–3 plants carrying an empty vector still displayed the mutant phenotype of small leaves (FIG. 6B). RNA gel blot analysis indicated that the phenotype correlated with ARGOS expression level in these plants (FIG. 6C). This finding, together with the observation that ARGOS induction by NAA was blocked in axr1, suggests that ARGOS functions downstream of AXR1 to mediate auxin-related cell proliferation and organ growth. Interestingly, the reduced lateral root development in axr1–3 seedlings was not rescued by over-expressing ARGOS (data not shown).

DISCUSSION

ARGOS Defines a Novel Gene Involved in Plant Development: Using a DNA microarray approach, we identified ARGOS gene whose expression was highly induced by auxin. Further characterization of sense and antisense transgenic plants shows that ARGOS is involved in the regulation of cell proliferation during organ development, thereby affecting plant organ size. Only one putative homolog is present in recently disclosed rice genome, suggesting that ARGOS might be plant specific. The *Arabidopsis* genome contains another putative gene sharing some sequence homology with ARGOS, but its expression pattern is different from that of ARGOS (unpublished data) and its function remains unknown. Therefore, our studies on ARGOS uncover a novel gene that plays an important role in plant growth and development.

ARGOS Regulates ANT-mediated Organ Size Control: Our data suggest that ARGOS is a novel gene involved in ANT-mediated organ size control. First, under- or over-expression of ARGOS and loss- or gain-of-function of ANT show similar phenotypic changes in aerial parts, which are caused by alterations in the duration of cell proliferation. Interestingly, although ARGOS and ANT are expressed in root, root phenotype was not observed either in early developmental stages of ARGOS transgenic plants, or in loss- or gain-of-function of ANT plants. Second, prolonged expression of CycD3;1 and neoplasia were observed both in over-expressed ARGOS and ANT leaf explants. Recent study on ectopically expressed CycD3;1 plants has suggested that CycD3;1 acts downstream of ANT to determine leaf cell number (Dewitte et al., 2003). The prolonged expression of ANT is observed in fully expanded 35S-ARGOS leaves, and loss of function of ANT blocked the enlarged organs in 35S-ARGOS plants. All these results are consistent with the notion that ARGOS is involved in the regulation of ANT-mediated organ size and acts upstream of ANT.

Figure 6:
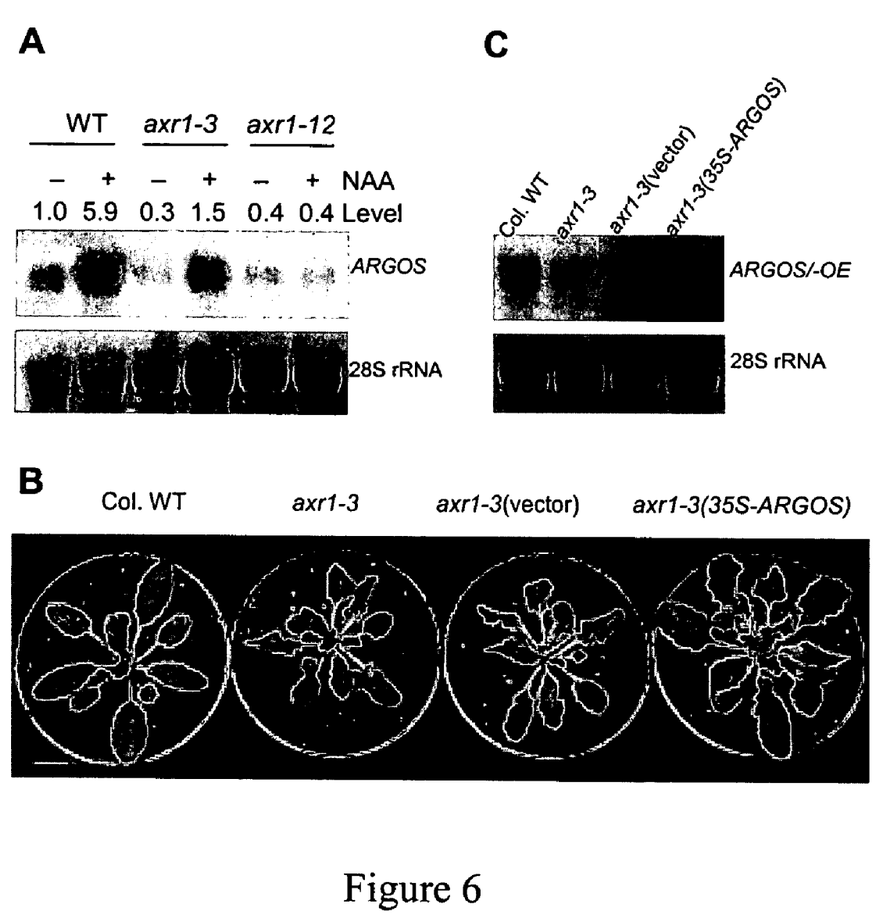
FIG. 6A: ARGOS expression in wild type, axr1–3 and axr1–12 plants with/without auxin treatment. RNAs were extracted from 12 day-old seedlings treated with 5 μM NAA (+) or H$_2$O (-) for 3 hours. Numbers above lanes refer toARGOS expression levels relative to the 28S rRNA levels.
FIG. 6B: 3 week-old plants of WT (Col.) axr1–3, transgenic axr1–3 carrying an empty vector and transgenic axr1–3 carrying a 35S-ARGOS transgene. Bar=10 mm.
FIG. 6C: Endogenous ARGOS mRNA and transgenic ARGOS (ARGOS-OE) mRNA levels in WT, axr1–3, axr1–3 (vector) and axr1–3 (35S-ARGOS).

ARGOS Mediates Auxin Signal to Affect Lateral Organ Development: Our observations that under- or over-expression of ARGOS altered cell proliferation and thus organ size, indicate that ARGOS is involved in the control of cell division-related organ development. The high induction of ARGOS by auxin suggests that ARGOS mediates auxin signaling. These results provide molecular evidence that auxin influences cell proliferation during organ development, though this process is difficult to mimic by application of exogenous auxin. The involvement of ARGOS in auxin signaling is further strengthened by the finding that ARGOS induction by auxin is attenuated or abolished in axr1 mutants and over-expression of ARGOS partially restores organ growth in axr1–3 mutant (FIG. 6). AXR1 is a component of the ubiquitin-activating enzyme E1 (Leyser et al., 1993), which functions in an early step of auxin signaling (Leyser, 2002) and may also mediate other plant signals, such as jasmonate and light (Schwechheimer et al., 2002; Xu et al., 2002).

BIBLIOGRAGHY

Autran, D., Jonak, C., Belcram, K., Beemster, G. T. S., Kronenberger, J., Grandjean, O., Inzé, D., and Traas, J. (2002). Cell numbers and leaf development in *Arabidopsis*: a functional analysis of the STRUWWELPETER gene. EMBO J. 21, 6036–6049.

Beemster, G. T. S., Fiorani, F., and Inzé, D. (2003). Cell cycle: the key to plant growth control? Trends Plant Sci. 8, 154–158.

Betchtold, N., Ellis, J., and Pelletier, G. (1993). In planta *Agrobacterium*-mediated gene transfer by infiltration of *Arabidopsis thaliana* plants. C.R. Acad. Sci. Paris 316, 1194–1199.

Casimiro, I., Marchant, A., Bhalerao, R. P., Beeckman, T., Dhooge, S., Swarup, R., Graham, N., Inzé, D., Sandberg, G., Casero, P. J., and Bennett, M. (2001). Auxin transport promotes *Arabidopsis* lateral root initiation. Plant Cell 13, 843–852.

Church, G. M. and Gilbert, W. (1984). Genomic sequencing, Proc. Natl. Caad. Sci. USA 81, 1991–1995.

Davies, P. J. (1995). The plant hormones: their nature, occurrence and functions. In Plant Hormones: Physiology, Biochemistry and Molecular Biology, P. J. Davies, ed (Dordrecht, Netherland: Kluwer Academic Publisher), pp. 1–12.

De Veylder, L., Beeckman, T., Beemster, G. T., de Almeida Engler, J., Ormenese, S., Maes, S., Naudts, M., Van Der Schueren, E., Jacqmard, A., Engler, G., and Inzé, D. (2002). Control of proliferation, endoreduplication and differentiation by the *Arabidopsis* E2Fa-DPa transcription factor, EMBO J. 21, 1360–1368.

Dewitte, W., Riou-Khamlichi, C., Scofield, S., Healy, J. M. S., Jacqmard, A., Kilby, N. J. and Murray, J. A. H. (2003). Altered cell cycle distribution, hyperplasia, and inhibited differentiation in *Arabidopsis* caused b the D-type cyclin CycD3. Plant Cell 15, 79–92.

Dharmasiri, S. and Estelle, M. (2002). The role of regulated protein degradation in auxin response. Plant Mol. Biol. 49, 401–409.

Doemer, P., Jogensen, J. E., You, R., Steppuhn, J., and Lamb, C. (1996). Control of root growth and development by cyclin expression. Nature 380, 520–523.

Donnelly, P. M. Bonetta, D., Tsukaya, H., Dengler, R. E., and Dengler, N. G. (1999). Cell cycling and cell enlargement in developing leaves of *Arabidopsis*. Dev. Biol. 215, 407–419.

Ecker, J. R. (1995). The ethylene signal transduction pathway in plant. Science 268, 667–675.

Elliott, R. C., Betzner, A. S. Huttner, E., Oakes, M. P., Tucker, W. Q., Gerentes D., Perez, P., and Smyth, D. R. (1996). AINTEGUMENTA, an APETALA2-like gene of *Arabidopsis* with pleiotropic roles in ovule development and floral organ growth. Plant Cell 8, 155–168.

Ferreira, P. C. G., Hemerly, A. S., de Almeida Engler, J., van Montagu, M., Engler, G., and Inzé, D. (1994). Developmental expression of the *Arabidopsis* cyclin gene cyc1At. Plant Cell 6., 1763–74.

Golz, J. F. and Hudson, A. (2002). Signaling in plant lateral organ development. Plant Cell 14, S277–S288.

Gray, W. M., del Pozo, J. C., Walker, L., Hobbie, L., Risseeuw, E., Banksm, T., Crosby, W. L., Yang, M., Ma, H., and Estelle, M. (1999). Identification of an SCF ubiquitin-ligase complex required for auxin response in *Arabidopsis thaliana*. Genes Dev. 13, 1678–1691.

Gray, W. M., Kepinski, S., Rouse, D., Leyser, O., and Estelle, M. (2001). Auxin regulates SCF—$^1$-dependent degradation of AUX/IAA proteins. Nature 414, 271–276.

Hemerly, A., de Almeida Engler J., Bergounioux, C., van Montagu, M., Engler, G., Inzé, D., and Ferreira, P. (1995). Dominant negative mutants of the Cdc2 kinase uncouple cell division from iterative plant development. EMBO J. 14, 3925–3936.

Hemerly, A. S., Ferreira, P., de Almeida Engler, J., van Montagu, M., Engler, G., and Inzé, D. (1993). Cdc2a expression in *Arabidopsis* is linked with competence for cell division. Plant Cell 5, 1711–1723.

Hu, Y., Bao, F., and Li, J. (2000). Promotive effect of brassinosteroids on cell division involves a distinct CycD3-induction pathway. Plant J. 24, 693–701.

Kepinski, S. and Leyser, O. (2002). Ubiquitination and auxin signaling: a degrading story. Plant Cell 14, S81–S95.

Kim, G. T, Shoda, K., Tsuge, T., Cho, K. H., Uchimiya, H., Yokoyama, R., Nishitani, K., and Tsukaya, H. (2002). The ANGUSTIFOLIA gene of *Arabidopsis*, a plant CtBP gene, regulates leaf-cell expansion, the arrangement of cortical microtubules in leaf cells and expression of a gene involved in cell-wall formation. EMBO J. 21, 1267–1279.

Kim, G. T., Tsukaya, H., and Uchimiya, H. (1998). The ROTUNDIFOLIA3 gene of *Arabidopsis thaliana* encodes a new member of the cytochrome P-450 family that is required for the regulated polar elongation of leaf cells. Genes Div. 12, 2381–2391.

Klucher, K. M., Chow, H., Reiser, L., and Fischer, R. L. (1996). The AINTEGUMENTA gene of *Arabidopsis* required for ovule and female gametophyte development is related to the floral homeotic gene APETALA2. Plant Cell 8, 137–153.

Kondorosi, E., Roudier, F., and Gendreau, E. (2000). Plant cell-size control: growing by ploidy, Curr. Opin. Plant Biol, 3, 488–492.

Kost, B., Spielhofer, P., and Chua, N. H. (1998). A CFP-mouse talin fusion protein labels plant actin filaments in vivo and visualizes the actin cytoskeleton in growing pollen tubes. Plant J. 16, 393–401.

Krizek, B. A. (1999). Ectopic expression of AINTEGUMENTA in *Arabidopsis* plants result in increased growth of floral organs. Dev. Genet. 25, 224–236.

Leu, W. M., Cao, X. L., Wilson, T. J., Snustad, D. P., and Chua, N. H. (1995). Phytochrome A and phytochrome B mediate the hypocotyl-specific down-regulation of TUB1 by light in *Arabidopsis*. Plant Cell 7, 2187–2196.

Leyser, H. M., Lincoln, C. A., Timpte, C., Lammer, D., Turner, J., and Estelle, M. (1993). *Arabidopsis* auxin-resistance gene AXR1 encodes a protein related to ubiquitin-activating enzyme E1. Nature 364, 161–1644.

Leyser, O. (2001). Auxin. Curr. Biol. 11, R728.

Leyser, O. (2002). Molecular genetics of auxin signaling. Annu. Rev. Plant Biol. 53, 377–398.

Lincoln, C., Britton, J. H., and Estelle, M. (1990). Growth and development of the axr1 mutants of *Arabidopsis*. Plant Cell 2, 1071–1080.

Meyerowitz, E. M. (1997). Genetic control of cell division patterns in developing plants. Cell 88, 299–308.

Mizukami, Y. (2001). A matter of size: developmental control of organ size in plants. Curr. Opin. Plant Biol. 4, 533–539.

Mizukami, Y. and Fischer, R. L. (2000). Plant organ size control: AINTEGUMENTA regulates growth and cell numbers during organogenesis. Proc. Natl. Acad. Sci. USA 97, 942–947.

Oakenfull, E. A., Riou-Khamlichi, C., and Murray, J. A. H. (2002). Plant D-type cyclins and the control of GI progression. Phil. Trans. R. Soc. Lond. B 357, 749–760.

Potter, C. J. and Xu, T. (2001). Mechanism of size control. Curr. Opin. Genet. Dev. 11, 279–286.

Riou-Khamlichi, C., Huntley, R., Jacqmard, A., and Murray, J. A. H. (1999). Cytokinin activation of *Arabidopsis* cell division through a D-type cyclin. Science 283, 1541–1544.

Schwechheimer, C., Serino, G., and Deng, X. W. (2002). Multiple ubiquitin ligase-mediated processes require COP9 signalosome and AXR1 function. Plant Cell 14, 2553–2563.

Talbert, P. B., Adler, H. T., Parks, D. W., and Comai, L. (1995). The REVOLUTA gene is necessary for apical meristem development and for limiting cell divisions in the leaves and stems of *Arabidopsis thaliana*. Development 121, 2723–2735.

Timpte, C. C., Wilson, A. K., and Estelle, M. (1992). Effects of the axr2 mutation of *Arabidopsis* on cell shape in hypocotyl and inflorescence. Planta 188, 271–278.

Tsuge, T., Tsukaya, H., and Uchimiya, H. (1996). Two independent and polarized processes of cell elongation regulate leaf blade expansion in *Arabidopsis thaliana* (L.) Heynh. Development 122, 1589–1600.

Tsukaya, H. (2002). Leaf development. In the *Arabidopsis* Book, C. R. Somerville and E. M. Meyerowitz, eds (Rockville, Md.: American Society of Plant Biologists), doi/10.1199/tab.0072, http:/www.aspb.org/publications/arabidopsis.

Van Lijsebettens, M. and Clarke, J. (1998). Leaf developments in *Arabidopsis*. Plant Physiol. Biochem. 36, 47–60.

Waites, R., Selvadurai, H. R. N, Oliver, I. R., and Hudson, A. (1998). The PHANTASTICA gene encodes a MYB transcription factor involved in growth and dorsoventrality of lateral organs in Antirrhinum. Cell 93, 779–789.

Weigel, D. and Jügens, G. (2002). Stem cells that make stems. Nature 415, 751–754.

Xie, Q., Frugis, G. Colgan, D., and Chua, N. H. (2000). *Arabidopsis* NACI transduces auxin signal downstream of TIRI to promote lateral root development. Genes Dev. 14, 3024–3036.

Xie, Q, Guo, H. S., Dallman, G., Fang, S., Weissman, A. M., and Chua, N. H. (2002). SINATS promotes ubiquitin-related degradation of NACI to attenuate auxin signals. Nature 419,167–170.

Xu, L., Liu, F., Lechner, E., Genschik, P., Crosby, W. L., Ma, H., Peng, W., Huang, D., and Xie, D. (2002). The $SCF^{con}$ ubiquitin-ligase complexes are required for jasmonate response in *Arabidopsis*. Plant Cell 14, 1919–1935.

Zhong, R. and Ye, Z. H. (1999). IFL1, a gene regulating interfascicular fiber differentiation in *Arabidopsis*, encodes a homeodomain-leucine zipper protein. Plant Cell 11, 2139–2152.

Zhong, R. and Ye, Z. H. (2001). Alteration of auxin polar transport in the *Arabdopsis* ifl1 mutants. Plant Physiol. 126, 549–563.

What is claimed is:

1. An isolated nucleic acid selected from the group consisting of:
   (a) a nucleic acid comprising the nucleotide sequence set forth in SEQ ID NO: 1; and
   (b) a nucleic acid comprising a nucleotide sequence that encodes the amino acid sequence of SEQ ID NO: 2.

2. The isolated nucleic acid of claim 1, wherein the nucleic acid is DNA.

3. The isolated nucleic acid of claim 2, wherein the nucleic acid is a cDNA.

4. The isolated nucleic acid of claim 2, wherein the nucleic acid is a genomic DNA.

5. The isolated nucleic acid of claim 1, wherein the nucleic acid is RNA.

6. The isolated nucleic acid of claim 5, wherein the nucleic acid is mRNA.

7. The isolated nucleic acid of claim 1, wherein the nucleic acid is a fusion gene.

8. A vector comprising the nucleic acid of claim 1 operably linked to a promoter that controls expression in a plant cell.

9. The vector of claim 8, wherein the promoter is a 35S promoter.

10. A method of enhancing organ development in a plant, comprising:
   transforming a plant cell with a nucleotide sequence operably linked to a promoter that controls expression in a plant cell, wherein the nucleotide sequence is selected from the group consisting of:
   (a) a nucleic acid comprising the nucleotide sequence set forth in SEQ ID NO:1; and
   (b) a nucleic acid comprising a nucleotide sequence that encodes the amino acid sequence of SEQ ID NO:2; cultivating the cell into a plant and expressing the nucleic acid sequence so that organ development is enhanced.

11. The method of claim 10, wherein the promoter is a 35S promoter.

12. The method of claim 10, wherein the plant is *Arabidopsis*.

13. The method of claim 10, wherein the organ is a lateral organ.

14. The method of claim 13, wherein the lateral organ is a leaf.

15. The method of claim 14, wherein the leaf is a rosette leaf.

16. The method of claim 10, wherein the organ development is organ growth.

17. The method of claim 16, wherein the growth is enhanced by about 50% to about 120%, as compared to a wild-type plant.

18. The method of claim 10, wherein the organ is a floral organ, an inflorescence stem, or a silique.

19. The method of claim 10, wherein the enhanced development is a longer hypocotyl in a de-etiolated seedling of the plant, as compared to a wild-type plant.

20. The method of claim 10, wherein the enhanced development is delayed flowering, as compared to a wild-type plant.

21. The method of claim 10, wherein the enhanced development is an increase in seed number in a silique of the plant, as compared to a wild-type plant.

22. The method of claim 16, wherein the enhanced organ growth is a result of increased cell number, as compared to a wild-type plant.

23. The method of claim 10, wherein the enhanced development is extension of growth duration.

24. The method of claim 23, wherein the extension is due to extended cell proliferation.

25. A transformed plant cell having stably incorporated into its genome a nucleotide sequence operably linked to a promoter that controls expression in a plant cell, wherein the nucleotide sequence is selected from the group consisting of:
   (a) a nucleic acid comprising the nucleotide sequence set forth in SEQ ID NO:1; and
   (b) a nucleic acid comprising a nucleotide sequence that encodes the amino acid sequence of SEQ ID NO:2.

26. The cell of claim 25, wherein the promoter is a 35S promoter.

27. The cell of claim 25, wherein the plant is *Arabidopsis*.

28. A transgenic plant having stably incorporated into its genome a nucleotide sequence operably linked to a promoter that controls expression in a plant cell, wherein the nucleotide sequence is selected from the group consisting of:
   (a) a nucleic acid having the nucleotide sequence set forth in SEQ ID NO;1; and
   (b) a nucleic acid having a nucleotide sequence that encodes the amino acid sequence of SEQ ID NO:2.

29. The plant of claim 28, wherein the promoter is a 35S promoter.

30. The plant of claim 28, wherein the plant is *Arabidopsis*.

31. A transgenic seed of the plant of claim 28, wherein the seed comprises the nucleotide sequence.

32. A method of regulating organ development in a plant, comprising transforming a plant cell with a nucleotide sequence operably linked to
   a promoter that controls expression in a plant cell, wherein the nucleotide sequence is selected from the group consisting of:
   (a) a nucleic acid comprising the nucleotide sequence set forth in SEQ ID NO:1; and
   (b) a nucleic acid comprising a nucleotide sequence that encodes the amino acid sequence of SEQ ID NO:2;
   cultivating the cell into a plant, whereby the nucleotide sequence is expressed and organ development is regulated.

33. The method of claim 32, wherein the promoter is a 35S promoter.

34. The method of claim 32, wherein the plant is *Arabidopsis*.

35. The method of claim 32, wherein the organ is a lateral organ.

36. The method of claim 32, wherein the organ development is organ growth.

37. The method of claim 32, wherein the organ is a floral organ, an inflorescence stem, or a silique.

38. The method of claim 32, wherein the regulated organ development is a result of altered cell division.

39. The method of claim 32, wherein the organ development is organ cell proliferation.

40. The method of claim 32, wherein the regulated organ development is a result of altered cell number.

* * * * *

```
                              SEQUENCE LISTING

<160> NUMBER OF SEQ ID NOS: 2

<210> SEQ ID NO 1
<211> LENGTH: 732
<212> TYPE: DNA
<213> ORGANISM: Arabidopsis thaliana
<220> FEATURE:
<221> NAME/KEY: CDS
<222> LOCATION: (388)..(708)

<400> SEQUENCE: 1
ttgtcttcct catttcccta ctagtacttg tttcacacag tttcttgatc caaccaaaac     60
caatacacaa agcttctcaa actccttcac ctcaaagctt cttcctttac atctgaatcg    120
ttgagttaac tcggatttgt tctgcatcct ctgtttctga atcgtgggcc atccttattt    180
```

```
tgtctcgaat tcttcaccaa ttgcttcgat caagctgcat tggttaacca gttgccctaa      240
agatcagatc tttgagcaaa attttgtcac tgatcttcta aatccaaacc agacacagca      300
aaacaacctc tgtagatgat tcgagaaatc tcaaacttac aaaagatat tataaacatt       360 caagacagtt attcgaacaa ccgagtc atg gac gtc gga aga aac aac cgg aaa      414
                               Met Asp Val Gly Arg Asn Asn Arg Lys
                                 1               5 aac atg agc ttt cga agt tcg ccg gag aaa agc aag caa gag tta cgg        462
Asn Met Ser Phe Arg Ser Ser Pro Glu Lys Ser Lys Gln Glu Leu Arg
 10              15                  20                  25 cgg agt ttc tcg gcg cag aaa agg atg atg atc ccg gcg aat tat ttc        510
Arg Ser Phe Ser Ala Gln Lys Arg Met Met Ile Pro Ala Asn Tyr Phe
                 30                  35                  40 agt tta gag tct ctg ttc cta ttg gtt ggt cta acg gca tct ctg tta        558
Ser Leu Glu Ser Leu Phe Leu Leu Val Gly Leu Thr Ala Ser Leu Leu
             45                  50                  55 ata ctt ccg tta gtt ttg ccg ccg tta cct ccg cct ccg ttt atg ctg        606
Ile Leu Pro Leu Val Leu Pro Pro Leu Pro Pro Pro Pro Phe Met Leu
         60                  65                  70 cta ttg gtt ccc att ggg att atg gtt tta ctc gtc gtt ctt gcc ttc        654
Leu Leu Val Pro Ile Gly Ile Met Val Leu Leu Val Leu Ala Phe
 75                  80                  85 atg cct tct tct cat tct aat gct aat aca gat gta act tgc aat ttc        702
Met Pro Ser Ser His Ser Asn Ala Asn Thr Asp Val Thr Cys Asn Phe
 90                  95                 100                 105 atg taa atctgaaatt tattatatga tgat                                      732
Met
```

```
<210> SEQ ID NO 2
<211> LENGTH: 106
<212> TYPE: PRT
<213> ORGANISM: Arabidopsis thaliana

<400> SEQUENCE: 2

Met Asp Val Gly Arg Asn Asn Arg Lys Asn Met Ser Phe Arg Ser Ser
 1               5                  10                  15

Pro Glu Lys Ser Lys Gln Glu Leu Arg Arg Ser Phe Ser Ala Gln Lys
                 20                  25                  30

Arg Met Met Ile Pro Ala Asn Tyr Phe Ser Leu Glu Ser Leu Phe Leu
             35                  40                  45

Leu Val Gly Leu Thr Ala Ser Leu Leu Ile Leu Pro Leu Val Leu Pro
         50                  55                  60

Pro Leu Pro Pro Pro Phe Met Leu Leu Leu Val Pro Ile Gly Ile
65                  70                  75                  80

Met Val Leu Leu Val Leu Ala Phe Met Pro Ser Ser His Ser Asn
                 85                  90                  95

Ala Asn Thr Asp Val Thr Cys Asn Phe Met
                100                 105
```